United States Patent [19]

Allard et al.

[11] 4,456,003
[45] Jun. 26, 1984

[54] KNEE JOINT ORTHOSIS

[75] Inventors: Paul L. Allard, Montreal; Jacques R. Sibille, Ottawa, both of Canada

[73] Assignee: The Muscular Dystrophy Association of Canada, Toronto, Canada

[21] Appl. No.: 354,190

[22] Filed: Mar. 3, 1982

[30] Foreign Application Priority Data

Jan. 29, 1982 [CA] Canada .................................. 395257

[51] Int. Cl.³ .............................................. A61F 3/00
[52] U.S. Cl. ........................................ 128/80 F; 3/27
[58] Field of Search ...................... 128/80 F, 80 A, 88, 128/87 R, 83; 3/22, 26, 27, 28, 29

[56] References Cited

U.S. PATENT DOCUMENTS

| 1,847,823 | 3/1932 | Dresser | 128/88 X |
| 2,827,897 | 3/1958 | Pawlowski | 128/80 F |
| 2,883,982 | 4/1959 | Rainey | 128/80 F |
| 3,826,251 | 7/1974 | Ross | 128/80 F |
| 4,370,977 | 2/1983 | Mauldin et al. | 128/80 F |

FOREIGN PATENT DOCUMENTS

| 1230323 | 9/1960 | France | 128/80 F |
| 1391924 | 12/1965 | France | 128/80 F |

Primary Examiner—John D. Yasko
Attorney, Agent, or Firm—Sim & McBurney

[57] ABSTRACT

There is provided a knee-joint orthosis for persons whose legs are weak or unstable. The orthosis includes a first elongate member adapted to be secured along the lower leg below the knee, and a second elongate member adapted to be secured along the upper leg above the knee. The two elongate members are hinged together at a pivot location which, when the elongate members are secured to the leg, can be substantially aligned with the hypothetical pivot axis between the upper and lower leg. A tension member is secured between a first location which moves with the first member and a section location which moves with the second member, the force of the tension member acting along a line which is spaced from the pivot location and which is such that tension in the tension member increases as the leg is flexed. In this manner, the moment acting to extend the leg increases as the leg is flexed.

7 Claims, 10 Drawing Figures

KNEE JOINT ORTHOSIS

This invention relates generally to mechanical devices adapted to stabilize the knee-joint in persons afflicted with weakness or instability of that joint, and has to do particularly with a knee-joint orthosis which is especially designed for use by Duchenne muscular dystrophy patients, although it will be understood from what follows that its use is not restricted to cases of Muscular Dystrophy.

BACKGROUND OF THIS INVENTION

Conventional knee-ankle orthoses have been used for many years in the management of patients afflicted with lower-extremities instabilities. Due to its construction, the conventional knee-ankle orthosis maintains the leg in extension during gait and contributes to an increase in postural lumbar lordosis and thoracic kyphosis. This conventional form of orthosis is still currently prescribed for Duchenne muscular dystrophy patients at the latter stage of their precarious ambulatory period.

Gait analysis shows that the vertical hip oscillation of a Duchenne muscular dystrophy patient increases around 65% with the conventional braces, as compared to hip oscillation without the braces. Observation of the brace patient's gait show that, to perform a walking step, he has to swing forward and upward both his hip and the extended leg while his whole weight is borne by the other leg.

Observation further shows that the lateral trunk sway (i.e. the angle subtended by a straight line joining the neck to the hip joint and the vertical, during a gait cycle) of the conventionally braced patient has a range more than twice that of the unbraced patient. This can be explained again by the lack of knee flexion.

Furthermore, while standing in the braces the patient usually takes an arched position, leaning back his shoulders and bringing his hips forward. This increases the patient lumbar lordosis and thoracic kyphosis.

All of these conditions are related to the fact that the conventional knee-ankle orthoses are rigid static devices primarily designed to support the legs. They provide very limited assistance to the patient in his gait.

Prior art developments are exemplified by U.S. Pat. No. 3,026,869, issued Mar. 27, 1962, U.S. Pat. No. 1,851,241, issued Mar. 29, 1932 and U.S. Pat. No. 3,826,251, issued July 30, 1974.

GENERAL DESCRIPTION OF THIS INVENTION

In view of the aforementioned problems encountered by Duchenne muscular dystrophy patients in using conventional long leg braces, it is an aspect of this invention to provide an knee-point orthosis which provides resistance to leg flexure.

It is an aspect of a particular embodiment of this invention to provide an knee-joint orthosis adapted to provide a counter-balancing moment at the knee to resist leg flexure, but which is designed in such a way that the resisting moment can be removed, to allow the user to sit without any moment being applied at the knee.

Accordingly, this invention provides a knee-joint orthosis for persons whose legs are weak or unstable. The orthosis includes a first elongate member for securement along the lower leg below the knee, and a second elongate member for securement along the upper leg above the knee. The elongate members are hinged together at a pivot location which, when the elongate members are secured to the leg, can be substantially aligned with the hypothetical pivot axis between the thigh and the calf. A tension member is secured between a first location which moves with the first member and a second location which moves with the second member. The force of the tension member acts along a line which is spaced from the pivot location, and which is such that tension in the tension member increases as the leg is flexed, whereby the moment acting to extend the leg increases as the leg is flexed. The second location is on a cog member pivoted about the pivot location, the second location being spaced from the pivot location, and the second elongate member including means for rotating the cog member along with the second elongate member about the pivot location. The means just mentioned includes a dog pivoted to the second elongate member, the dog being pivotally mounted to move between (a) a first position in which it bears against the cog member and rotates the same along with the second elongate member, and (b) a second position in which it frees the cog member for movement independent of said second elongate member.

GENERAL DESCRIPTION OF THE DRAWINGS

One embodiment of this invention is illustrated in the accompanying drawings, in which like numerals denote like parts throughout the several views, and in which.

DETAILED DESCRIPTION OF THE DRAWINGS

Figure 1:
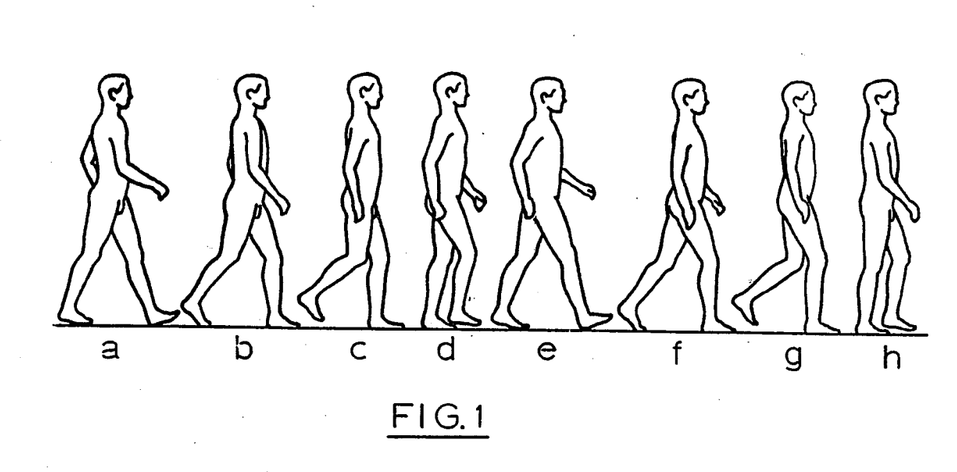
FIG. 1 shows a number of sequential side views of a person performing a complete gait cycle.

Attention is first directed to FIG. 1, illustrating eight sequential stages during normal walking gait. Noting the right leg of the walker, it will be seen that the right leg is substantially in extension in FIG. 1a (straightened out) at a point where the walker is preparing to lift the right leg and bring it forward for the next step. FIG. 1b shows the beginning of the lifting phase. The right heel is well off the ground, and the leg is beginning to flex at the knee. FIG. 1c shows maximum flexure at the knee, with the foot clear of the ground and being brought forward. FIG. 1d shows the leg going from a flexed to an extended position, while FIG. 1e shows right heel contact with the leg again substantially in extension. Weight is then transferred to the right leg, which typically supports the weight with the knee slightly bent as shown in FIGS. 1f and 1g. However towards the end of this phase, the right leg becomes straightened as the left leg is brought forward for the next step.

It is thus apparent that, for each cycle in the walking gait, the leg goes through two flexures and two extensions. The two extensions are shown in parts a and e of FIG. 1, while the two flexures are illustrated in parts c and g of FIG. 1. It will further be noted that during the flexure shown in FIG. 1c there is no weight placed on the leg, because the foot is in the air and the leg is being brought forward for the next step. By contrast, for the flexure shown in FIGS. 1f and 1g, the full weight of the body is on the leg. This means that the thigh muscle must resist complete flexure or collapse of the knee joint during the second flexure while the weight of the body is supported by the leg, whereas no resistance to flexure need be applied for the first flexure shown in FIG. 1c.

In attempting to design a knee-joint orthosis adapted to be of maximum assistance to a person whose lower extremities are weak or unstable, as in Duchenne muscular dystrophy patients, some means should be devised for mechanically resisting flexure of the leg in the phase represented by FIGS. 1f and 1g, but the resisting means should become inoperative during the flexure phase illustrated by FIGS. 1b and 1c. If the mechanical means were to resist flexure during the phase represented by FIGS. 1b and 1c, the leg would not remain in flexure, but would become straightened to extension and would result in a very awkward gait. This in fact happens with conventional leg braces which are designed to lock the knee in total extension.

Figure 2A:
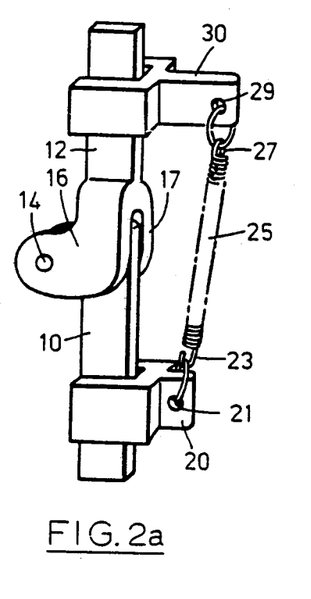
FIGS. 2a, 2b and 2c illustrate a schematic mechanism in sequential positions during flexure.
Figures 2B, 2C:
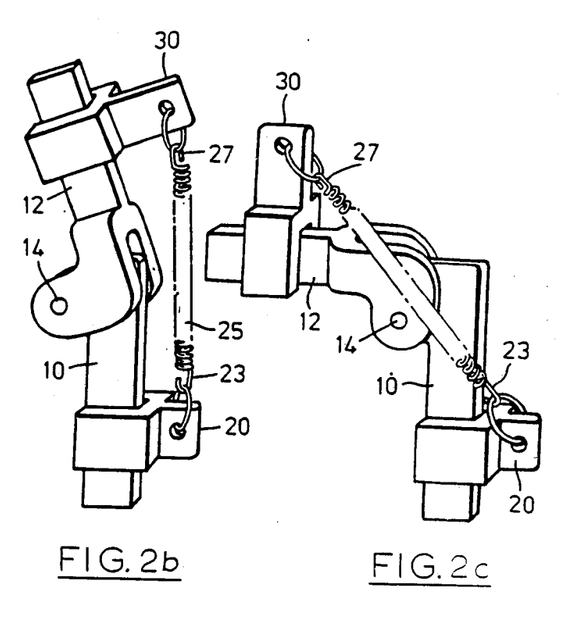

The basic principle of the invention is illustrated in FIGS. 2a, 2b and 2c. In FIG. 2a, the number 10 schematically represents a first elongate member adapted to be secured along the lower leg of the user, while the number 12 represents a second elongate member adapted to be secured along the upper leg of the user above the knee. As can be seen, the two elongate members 10 and 12 are hinged together at a pivot location 14, and it is understood that the pivot location can be substantially aligned with the hypothetical pivot axis in the upper and lower leg, when the elongate members are secured to the leg.

More specifically, the second or upper elongate member 12 is forked to define two brackets 16 and 17 which extend curvingly at approximate right angles to the main extent of the elongate member 12. Thus, the pivot location 14 is displaced leftwardly from the main position of the elongate number 12 as pictured in FIG. 2.

The first elongate member 10 also has a leftward extension (not visible in the Figures) which is slidingly received between the brackets 16 and 17, and which extends to the pivot location 14 where it is pivoted to the second elongate member 12.

At a location spaced from the pivot location 14, the first elongate number 10 has affixed thereto a bracket 20 defining an opening 21 to which is attached the lower end 23 of a tension member 25. The upper end 27 of the tension member 25 is connected to an opening 29 in a bracket 30 fixed with respect to the second member 12, again at a location spaced from the pivot location 14.

The position of the members 10 and 12 in FIG. 2a represents the extreme clockwise position of the member 12 with respect to the member 10. It is assumed in FIG. 2a that there is some tension in the tension member 25, and thus the latter would tend to keep the members 10 and 12 in the position shown in FIG. 2a.

If the members 10 and 12 were now secured to the calf and thigh of the leg, respectively, of a patient, with the patient facing rightwardly, then it can be seen that FIG. 2b would represent the beginning of flexure of the knee joint. It can also be realized that, as the member 12 pivots in the counter-clockwise direction with respect to the member 10, the tension member 25 begins to stretch, thus applying an increasing moment to resist the flexure.

When the knee has flexed to the sitting position, as represented by FIG. 2c, the tension member 25 has increased its force close to the maximum with the arrangement shown, however the distance from the pivot location 14 to the center line of the tension member 25, along which the force is exerted, has decreased progressively from FIG. 2a to FIG. 2c. Depending upon the spring constant, the degree of pretension in the tension number 25, and the position of the upper bracket 20 and lower bracket 30 this may result in the total moment seeking to resist flexure being smaller in FIG. 2c than it is, for example, in FIG. 2b or FIG. 2a. Thus, it would be possible to design a mechanical device of this kind which is such that the moment seeking to resist flexure of the knee joint drops to a low value when the patient reaches the sitting position.

While the structure illustrated schematically in FIGS. 2a–2c could be employed in an orthosis to resist knee flexure, and thus provide additional strength to the leg, and moreover could apply a resisting moment the value of which depended upon the angle of flexure, such a device would not, in itself, solve the problem described above with respect to FIG. 1, namely the desirability of applying a flexure-resisting moment during the flexure represented by FIG. 1g, but not during the flexure represented by FIG. 1c.

Figure 3:
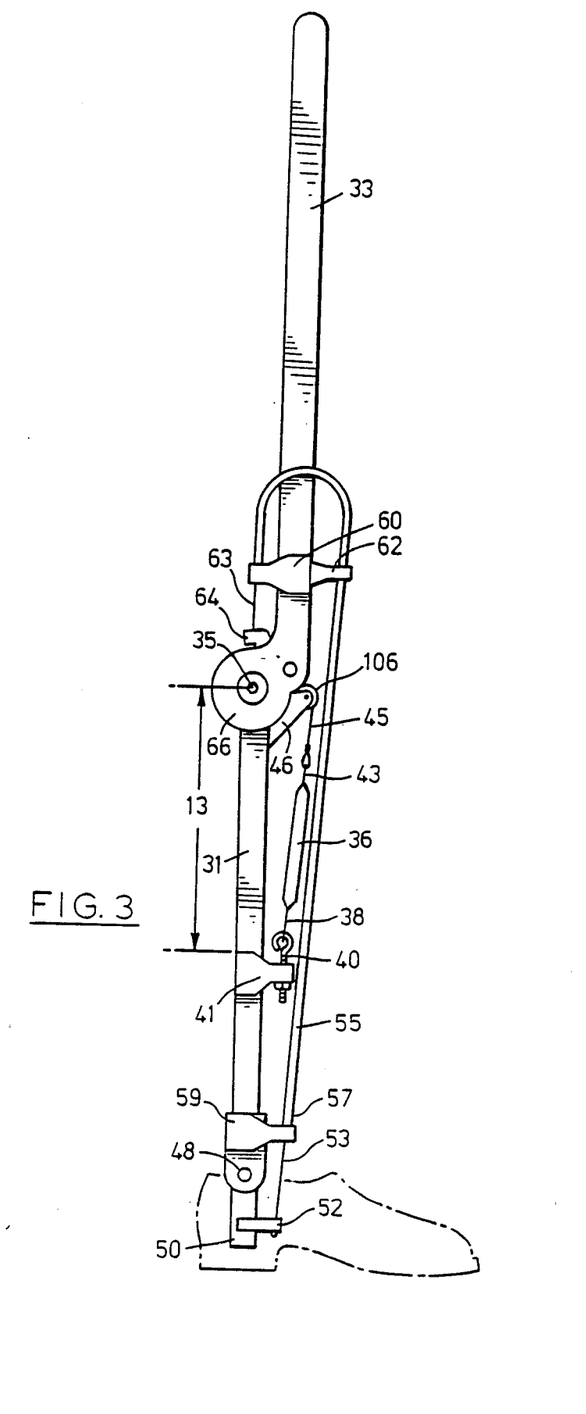
FIG. 3 is an elevational view of a knee-joint orthosis constructed in accordance with this invention.

To allow for such selective functioning, the device shown generally in FIG. 3 has been devised.

In FIG. 3, a first elongate member 31 is adapted to be secured along the calf of the user below the knee, while a second elongate member 33 is adapted to be secured along the thigh of the user above the knee. The two elongate members are hinged together at a pivot location 35 which, when the elongate members 31 and 33 are secured to the leg, can be substantially aligned with the hypothetical pivot axis between the upper and lower leg of the user.

A tension member 36 is provided to fill the function of tension member 25 in FIG. 2, and it can be seen that the lower end 38 of the tension member 36 is connected to an eye-bolt 40 which is adjustably secured on a bracket 41 which is fixed with respect to the elongate member 31. The upper end 43 of the tension member 36 is secured to a cable 45 which passes around a pulley mounted on a bracket 46, and which then extends leftwardly and is secured in a manner which will be described later with reference to FIGS. 4–7.

Pivotally connected at the location 48 at the bottom of the elongated member 31 is a foot brace 50 which is adapted to be connected with respect to the foot, typically by being secured to the shoe of the user, so that the foot brace 50 will swing or pivot as the user moves his foot about the ankle joint.

Secured to the member 50 is a bracket 52 extending forwardly, to which is affixed one end of the moveable cable 53 of a Bowden wire 55. A Bowden wire consists of a flexible cylindrical sheath of fixed length with a non-elastic cable extending slideably within it. By fixedly securing both ends of the sheath, the action of pulling one end of the cable out of the sheath at one end will cause the cable to be pulled into the sheath at the other end. This principle is used in multiple-speed bicycles for the operation of the hand brakes.

The lower end 57 of the sheath of the Bowden wire 55 is affixed to a bracket 59 at the bottom of the member 31, the bracket 59 extending forwardly. Affixed to the elongate member 33 is a further bracket 60 which extends rearwardly and to which the other end of the sheath of the Bowden wire 55 is secured. An additional steadying bracket 62 extends forwardly, and merely positions the Bowden wire in an out-of-the-way location so that it does not interfere with leg movement. As can be seen in FIG. 3, the other end 63 of the cable 53 extends downwardly below the bracket 60, and is secured to a dog 64 which will be described in greater detail with respect to FIGS. 4-7.

Still looking at FIG. 3, it will be understood that, as the foot brace 50 pivots in the clockwise direction about the pivot location 48, the cable 53 is pulled downwardly with respect to the sheath of the Bowden wire 55, thus causing the dog 64 to be pulled upwardly toward the bracket 60.

Figure 4:
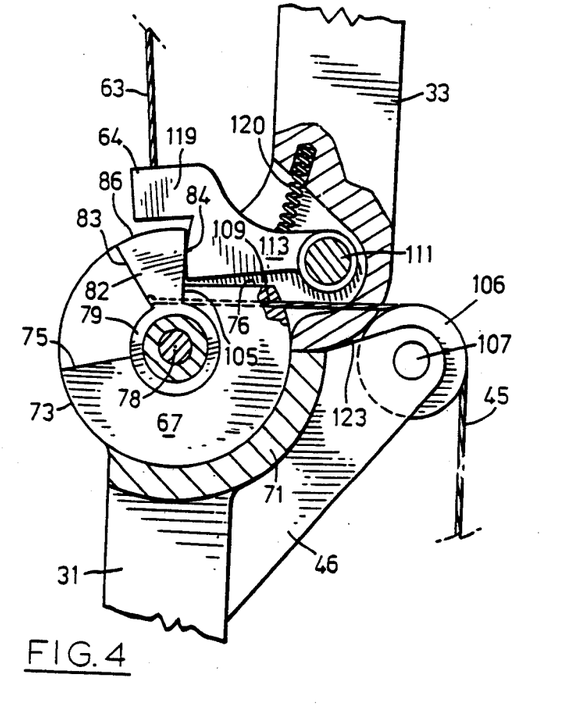
FIGS. 4, 5, 6 and 7 are views of the hinge location of the device shown in FIG. 3 to a larger scale, showing sequential steps during flexure.
Figure 8:
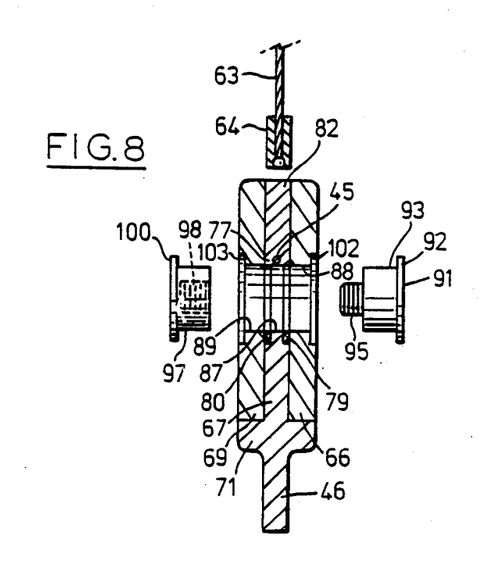
FIG. 8 is a sectional view taken at the line 8—8 in FIG. 5.

Attention is now directed to FIG. 4, which shows, to a larger scale, the hinge portion of the apparatus of FIG. 3. More specifically, the diagram of FIG. 4 is in a sense incomplete, in that it lacks one of the two pivot plates of the member 33 which normally hide the internal components which can be seen in FIG. 4. The member 33 is in fact bifurcated, and defines 2 pivot plates of which one is seen at 66 in FIG. 3, and of which the other is hidden behind the upper end 67 of the member 31 in FIG. 4. Each pivot plate at the bottom of the member 33 consists of a circular portion, and as can be seen in FIG. 8 the two pivot plates 66 and 69 are parallel and spaced from each other so as to allow entry of the upper portion 67 of the member 31. For clarity the upper end of the member 31 has been stippled so that its outline can be distinguished from other members which can be moved with respect thereto. Looking at FIGS. 4 and 8, the upper portion 67 is narrower than the main shank of the member 31, the main shank extending part way around the portion 67 to define portion 71. The portion 71 extends laterally to either side of the portion 67 as can be seen in FIG. 8.

The portion 67 is delimited by an arcuate surface 73, a rectilinear radial surface 75, a rectilinear upper surface 76, and an arched portion which extends between the inner ends of the surfaces 75 and 76, and which is concentric about the point 78 with the remainder of the portion 67. The arched portion is seen in FIG. 8 at the numeral 77, but is hidden in FIG. 4 by one of two rings 79 and 80 which extend downwardly from a wedged-shaped cog 82 which is defined by two radial edges 83 and 84, and by an outer arcuate edge 86. The cog 82 is sized to fit snugly but slideably between the pivot plates 66 and 69 which are part of the upper elongate member 33, and the rings 79 and 80 which are integral with the cog 82 are adapted to fit in opposed annular recesses immediately outwardly adjacent a bore 87 in the portion 67, the bore 87 being adapted for alignment with bores 88 and 89 in the pivot plates 66 and 69, respectively.

A bolt 91 having a head 92, a shoulder 93 and a threaded shank 95 is adapted to enter the alinged bores and screw into a cylindrical bolt 97 having a threaded bore 98 and a head 100. The heads 92 and 100 fit into recesses 102 and 103, respectively, and the recess 103 can be elongated or otherwise shaped so that, when the cylindrical bolt 97 is in place it will not rotate with respect to the pivot plate 69.

Figure 5:
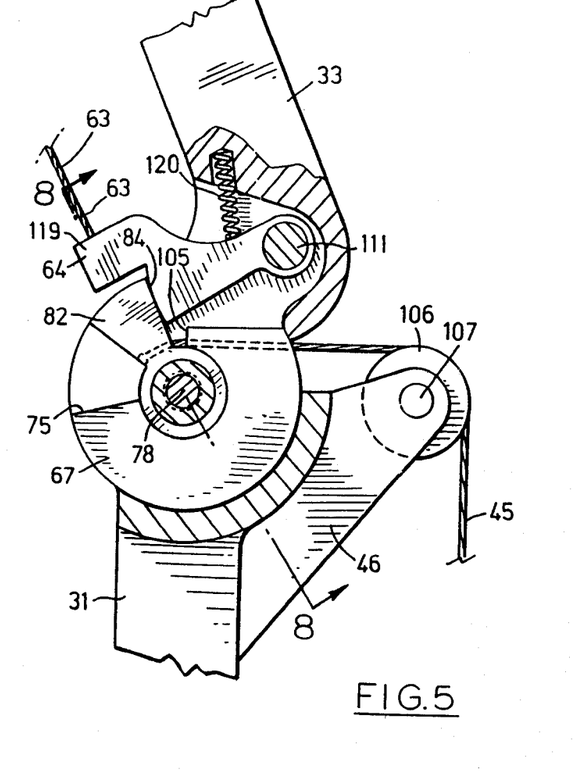

It will be seen in FIG. 5 that the portion 67 provides an abutment 105 for the cog 82 limiting clockwise movement, while the surface 75 limits counterclockwise movement thereof. Thus, the cog 82 is enabled to pivot between the positions shown in FIGS. 4 and 6. The cable 45 (seen first in FIG. 3) which is constantly pulled downwardly by the tension in the tension member 36, passes over a freely turning pulley 106 mounted on the bracket 46. The bracket 46 is affixed to the lower elongate member 31. A pin 107 provides the axis for the pullery 106. After passing over the pulley 106 the cable 45 then extends leftwardly, and passes through a bore 109 through which it can slidingly move, thence exiting at the leftward end of the abutment 105, passing below the solid portion of the cog 82 (i.e. between the cog 82 and the arched portion 77), and finally being secured to the cog 82 by being inserted into a small bore in its leftward edge (as pictured in FIG. 5) and welded, glued or otherwise cemented thereto.

Due to this arrangement, and the tension constantly exerted by the tension member 36, the cable 45 continually seeks to pull the cog 82 into the furthest clockwise position, which is that shown in FIG. 4, in which the cog 82 abuts against the abutment 105.

The dog 64 is pivoted inside the fork arrangement defined by the pivot plates 66 and 69, about a pivot pin 111, shown in section in the drawings. The dog 64 includes a shank 113, a curved abutment surface 114 (see FIG. 7), and a lever portion 119. The end 63 of the cable 53 is affixed to the lever portion 64, and it will be readily seen that an upward pull on the end 63 of the cable 53, arising due to clockwise swivelling of foot brace 50 during plantar flexion, will withdraw the dog 64 from the interfering relationship shown in FIG. 4, in which the abutment surface 114 of the dog 64 bears against the radial edge 84 of the cog 82.

A compression coil spring 120 is adapted to bias the dog 64 in the counter clockwise direction, i.e. into engagement or interfering relation with the cog 82.

Looking now sequentially at FIGS. 4 through 7, the operation of the knee-joint orthosis will be described.

FIG. 4 represents extension of the leg, in which the thigh and the calf are substantially aligned. While the cable 45 is exerting rightward tension of the cog 82, the latter is also in abutment with the abutment surface 105, and therefore cannot push rightwardly against the dog 64. In any event, in the position of FIG. 4, the lower portion 123 of the upper elongate member 33 is an engagement with the top of the portion 71, thus preventing further clockwise movement of the member 33 with respect to the member 31.

FIG. 5 shows the beginning of flexion, in which the upper member 33 has moved through a small angle in the counterclockwise sense with respect to the lower elongate member 31. In so doing, the dog 64 moves the cog 82 in the counter clockwise sense, thus pulling leftwardly on the cable 45 and stretching the tension member 36 (seen in FIG. 3). The moment being exerted by the cable 45 about the central axis 78 is the product of the force in the cable 45 times the distance from the pivot axis 78 to the line along which the force is exerted. In the early phase of flexion, the length of the moment arm will not substantially change, and therefore the increase in the tension of the cable 45 will cause an increased moment seeking to restore the members 31 and 33 to the FIG. 4 position, representing extension of the leg.

Figure 6:
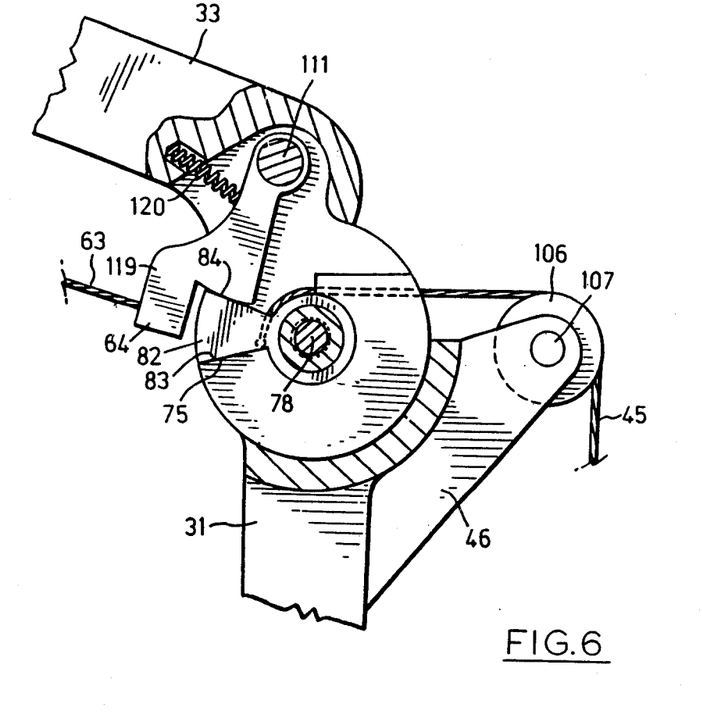

FIG. 6 shows a further stage of flexion of the knee joint, in which the cog 82 has moved around counter-clockwise to the limit position in which it abuts the abutment surface 75. So long as the dog 64 remains in engagement with the cog 82, the members 31 and 33 cannot move further toward flexion than the position shown in FIG. 6.

In order to allow this further degree of flexion (i.e. beyond that shown in FIG. 6), the dog 64 must be pulled out of interfering relation with respect to the cog 82, and this can be caused by tension in the end 63 of the cable 53, arising due to plantar flexion of the foot, which causes clockwise rotation of the foot brace 50 with respect to the pivot location 48 (see FIG. 3).

It is to be understood that it is not necessary for the members 31 and 33 to reach the FIG. 6 position before the dog 64 can be withdrawn from interfering relation. The withdrawal of dog 64 can take place at any time, merely by plantar flexion of the foot.

Figure 7:
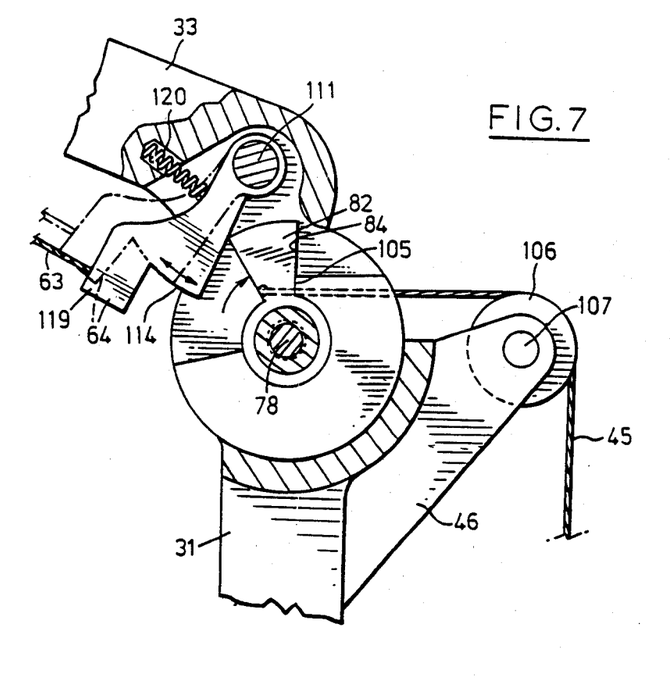

FIG. 7 shows in broken lines the position of the dog 64 when completely withdrawn from interfering relation with the cog 82, thus allowing the latter to return to its furthest clockwise position, which is the same as that shown in FIG. 4. The solid line position of the dog 64 in FIG. 7 represents the return of the dog 64 to its furthest counter-clockwise position (resting against the cog 82), due to the pressure from the compression spring 120.

Referring now to FIG. 1, and imaging that the wearer were using an orthosis as illustrated in FIGS. 3–8, the leg extension at FIG. 1a would correspond substantially to the arrangement of FIG. 4, in which, due to abutment between the cog 82 and the abutment surface 105, no pressure would be applied to the leg in the sense opposite that of flexure.

As the leg moved to the FIG. 1b position, the slight flexure would be resisted initially by the tension in the cable 45. However, as the patient pushes off from the foot before swinging it fowardly through the air, the foot would undergo plantar flexion (i.e. clockwise rotation with respect to the ankle joint), and this would withdraw the dog 64 from interfering relationship with respect to the cog 82. Hence, during the forward swing phase represented by FIGS. 1c and 1d, the joint would be in the condition of FIG. 7, in which the cable 45 is not applying restorative force to the joint, due to the fact that the dog 64 and the cog 82 are not in engagement.

Then, when the leg is again in extension at FIG. 1e, the dog 64 would fall in adjacent the face 84 of the cog 82, and engage it as shown in FIG. 4. Thereafter, during the slight flexion represented by FIGS. 1f and 1g, the tension in the cable 45 would be available to help support the leg as it bears the full weight of the wearer of the orthosis. It will be noted that there is no real possibility of moving the foot through plantar flexion in the stages represented by FIGS. 1f and 1g, and thereofre there is no likelihood that the dog 64 would be withdrawn from engagement with the cog 82.

While a specific embodiment of the invention has been described with reference to the drawings in the above disclosure, it will be apparent to those skilled in the art that changes and modifications may be made therein without departing from the scope of the invention as set forth in the appended claims.

We claim:

1. A knee-joint orthosis for persons whose legs are weak or unstable, comprising:

a first elongate member adapted to be secured along the lower leg below the knee, a second elongate member adapted to be secured along the upper leg above the knee, the two elongate members being hinged together at a pivot location which, when the elongate members are secured to the leg, can be substantially aligned with the hypothetical pivot axis between the upper and lower leg, and a tension member secured between a first location which moves with said first member and a second location which moves with said second member, the force of the tension member acting along a line which is spaced from the pivot location and which is such that tension in said tension member increases as the leg is flexed, whereby the moment acting to extend the leg increases as the leg is flexed, the second location being on a cog member pivoted about said pivot location, said second location being spaced from said pivot location, the second elongate member including means for rotating the cog member along with the second elongate member about said pivot location, said means including a dog pivoted to the second elongate member, the dog being pivotally mounted to move between (a) a first position in which it bears against said cog member and rotates the same along with the second elongate member, and (b) a second position in which it frees the cog member for movement independent of said second elongate member.

2. The orthosis claimed in claim 1, in which the tension member includes an elastic cord which is under pretension when the orthosis is in the position corresponding to leg extension.

3. The orthosis claimed in claim 1 or claim 2, which includes means restraining the two elongate members from pivoting from the extended position in the rotational sense opposite that corresponding to leg flexure.

4. The orthosis claim in claim 1 or claim 2, in which the two elongate members undergo mechanical interference when they are in the position corresponding to leg extension, and from such position can only mutually pivot in the direction corresponding to leg flexure.

5. The orthosis claimed in claim 1, which further includes control means by which a wearer of the orthosis can selectively move the dog from said first toward said second position.

6. The orthosis claimed in claim 5, in which said control means includes a pivotal foot brace at the bottom of the second elongate member, swingable by ankle motion, and a Bowden wire connected to allow pivotal motion of the foot brace in the direction of plantar flexion to move the dog from said first toward said second position.

7. The orthosis claimed in claim 1, in which the tension member includes a cable having one end connected to said cog member, the cable being entrained around a freely-rotating pulley and having its other end attached to one end of an elastic member, which in turn has its other end connected to an attachment point fixed with respect to the first elongate member and spaced below said pivot location between the elongate members.

* * * * *